(12) United States Patent
Zhang et al.

(10) Patent No.: US 11,389,427 B2
(45) Date of Patent: Jul. 19, 2022

(54) COMPOSITIONS AND METHODS OF TREATING CARDIAC HYPERTROPHY AND HEART FAILURE

(71) Applicants: CASE WESTERN RESERVE UNIVERSITY, Cleveland, OH (US); SAINT LOUIS UNIVERSITY, St. Louis, MO (US)

(72) Inventors: Lilei Zhang, Cleveland Heights, OH (US); Mukesh K. Jain, Solon, OH (US); Thomas Burris, Columbia, IL (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 3 days.

(21) Appl. No.: 16/485,359

(22) PCT Filed: Feb. 9, 2018

(86) PCT No.: PCT/US2018/017603
§ 371 (c)(1),
(2) Date: Aug. 12, 2019

(87) PCT Pub. No.: WO2018/148531
PCT Pub. Date: Aug. 16, 2018

(65) Prior Publication Data
US 2019/0374507 A1  Dec. 12, 2019

Related U.S. Application Data

(60) Provisional application No. 62/457,579, filed on Feb. 10, 2017.

(51) Int. Cl.
*A61K 31/4025* (2006.01)
*A61P 9/00* (2006.01)
*A61K 31/381* (2006.01)
*A61K 9/00* (2006.01)

(52) U.S. Cl.
CPC ........ *A61K 31/4025* (2013.01); *A61K 9/0019* (2013.01); *A61K 9/0053* (2013.01); *A61K 31/381* (2013.01); *A61P 9/00* (2018.01)

(58) Field of Classification Search
CPC .............. A61K 31/4025; A61K 9/0019; A61K 9/0053; A61K 31/381; A61P 9/00
See application file for complete search history.

(56) References Cited

U.S. PATENT DOCUMENTS

2012/0230978 A1* 9/2012 Eichele ................ A61K 31/713
536/23.1
2015/0038503 A1   2/2015 Bourotte et al.
2015/0031387 A1   11/2015 Li et al.

OTHER PUBLICATIONS

Solt et al. Regulation of circadian behaviour and metabolism by synthetic REV-ERB agonists. (Nature, vol. 485, May 3, 2012).*
Sitaula (BBRC vol. 460 pp. 566-571 published 2015). (Year: 2015).*
Ayala et al. "Attenuation of endoplasmic reticulum stress using the chemical chaperone 4-phenylbutyric acid prevents cardiac fibrosis induced by isoproterenol". Experimental and Molecular Pathology. 2012. vol. 92, pp. 97-104, entire document, especially: p. 97, col. 2, para 1; p. 103, col. 1, para 1.

* cited by examiner

*Primary Examiner* — Theodore R. Howell
*Assistant Examiner* — George W Kosturko
(74) *Attorney, Agent, or Firm* — Tarolli, Sundheim, Covell & Tummino LLP

(57) ABSTRACT

A method of treating cardiac hypertrophy and/or heart failure in a subject includes administering to the subject a therapeutically effective amount of a REV-ERBα agonist.

7 Claims, 4 Drawing Sheets

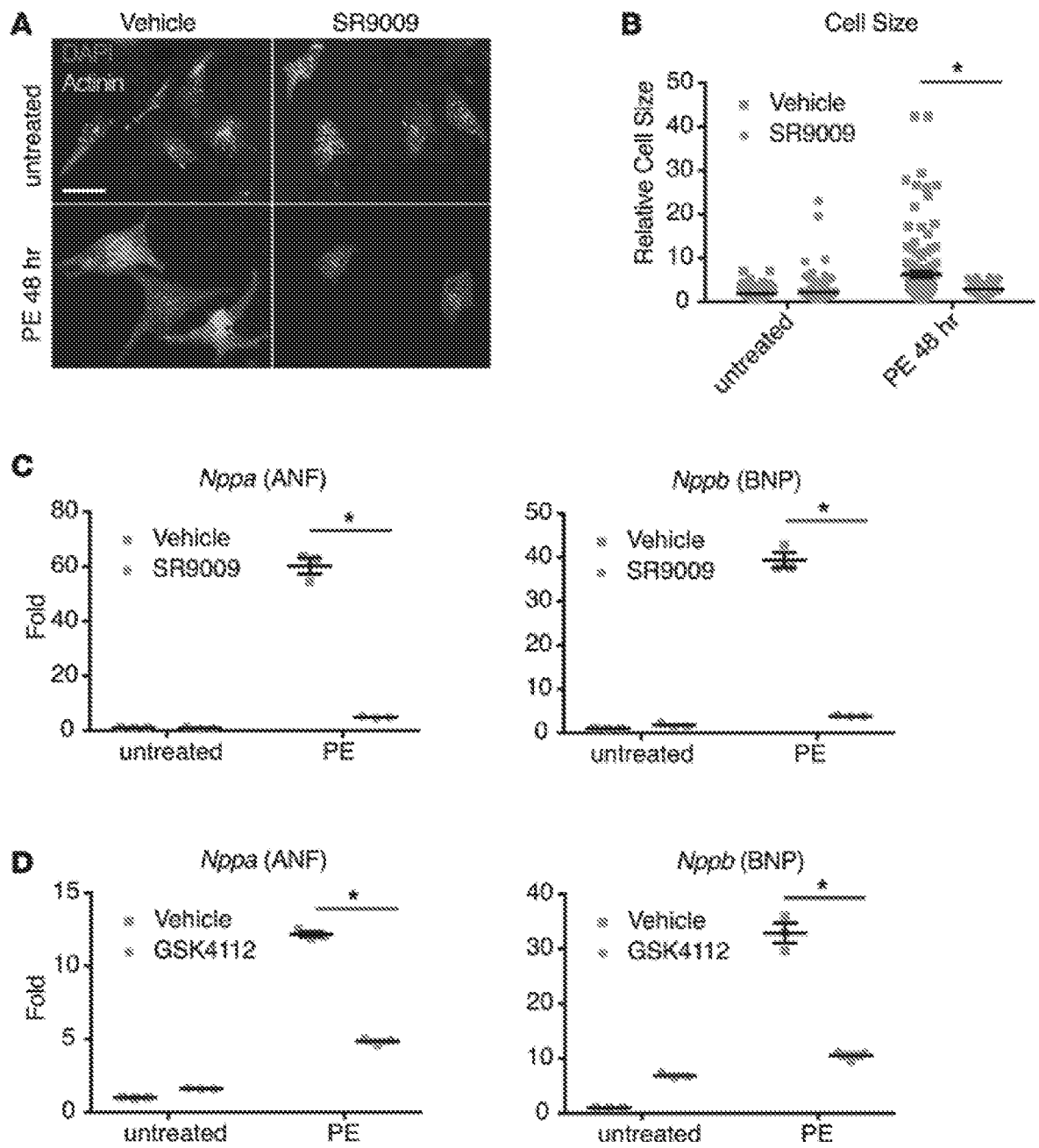
Figs. 1(A-D)

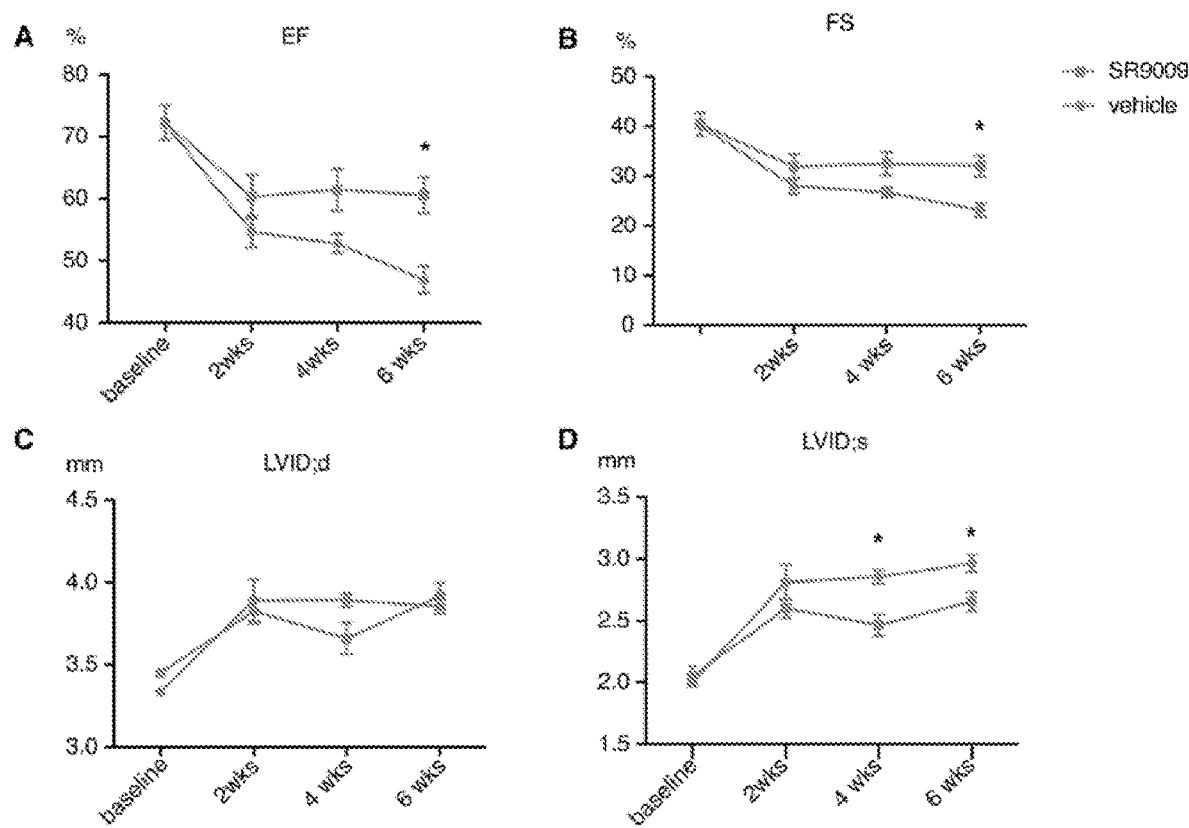
Figs. 2(A-D)

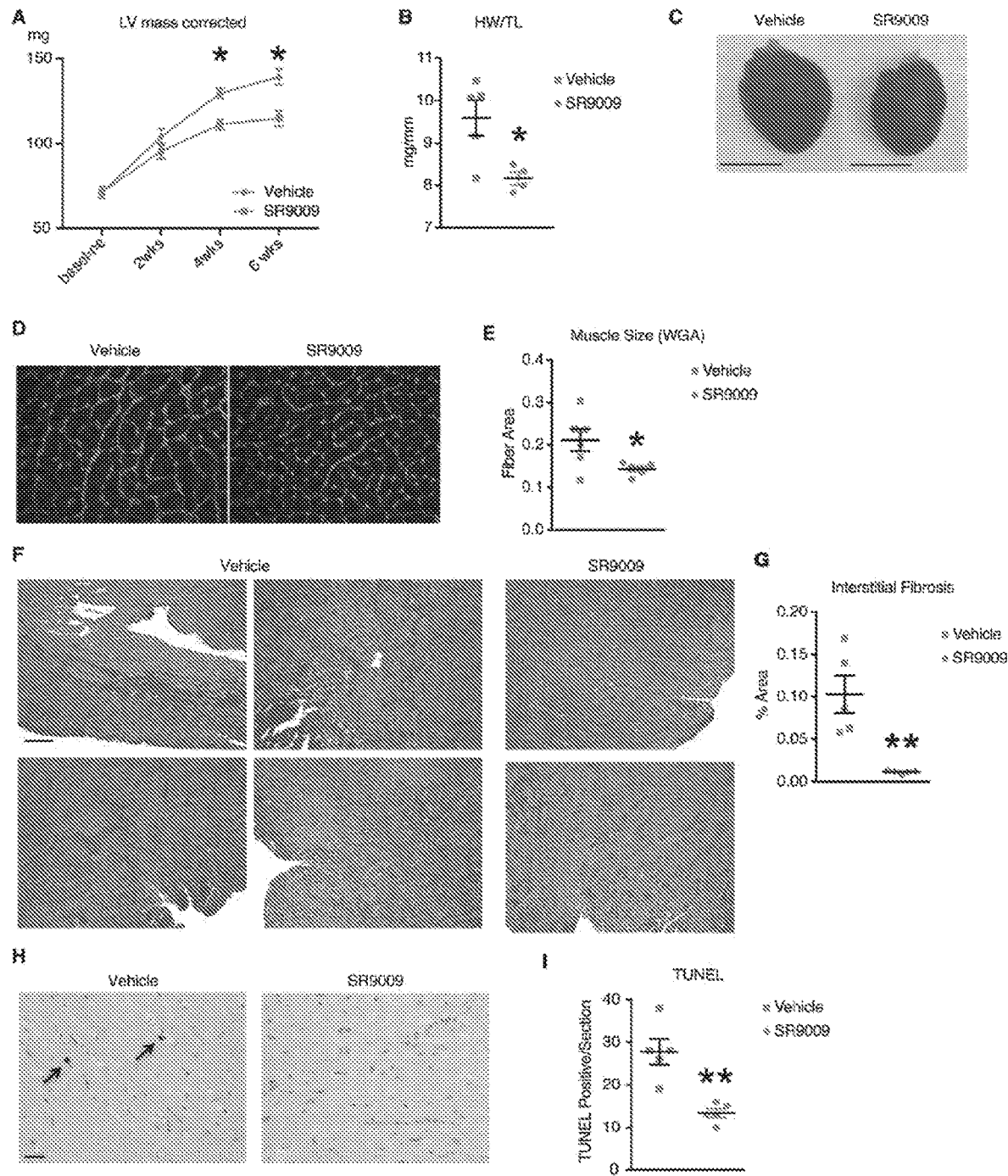
Figs. 3(A-I)

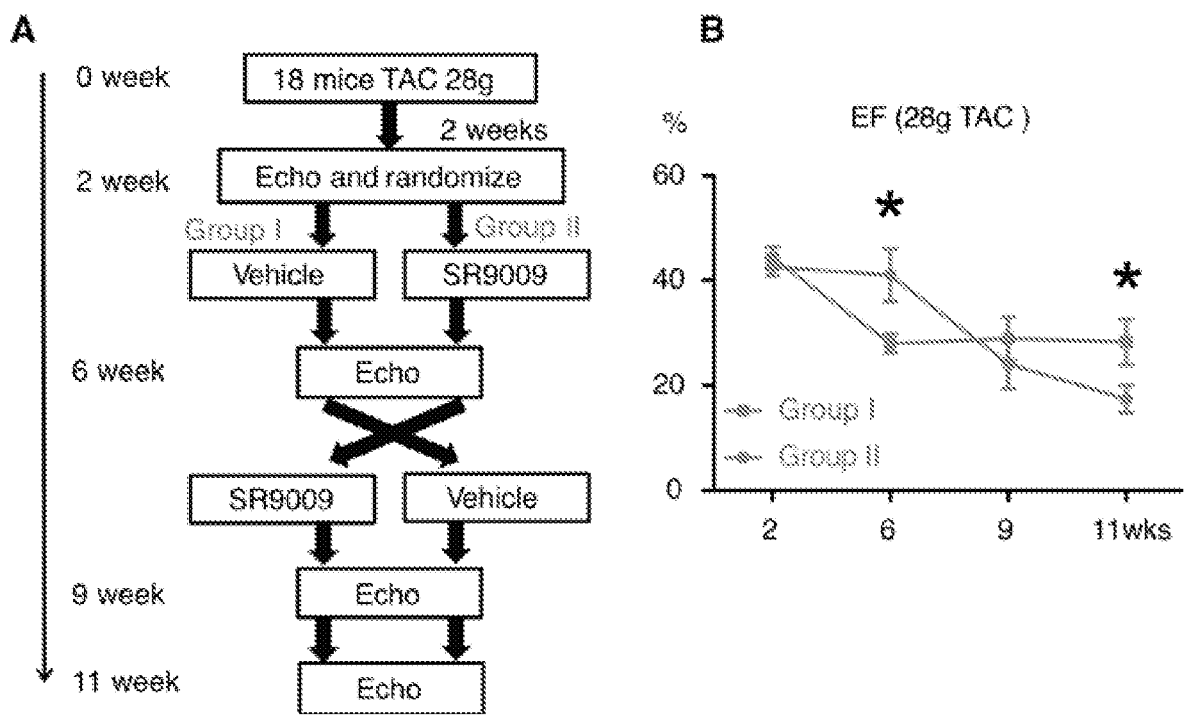
Figs. 4(A-B)
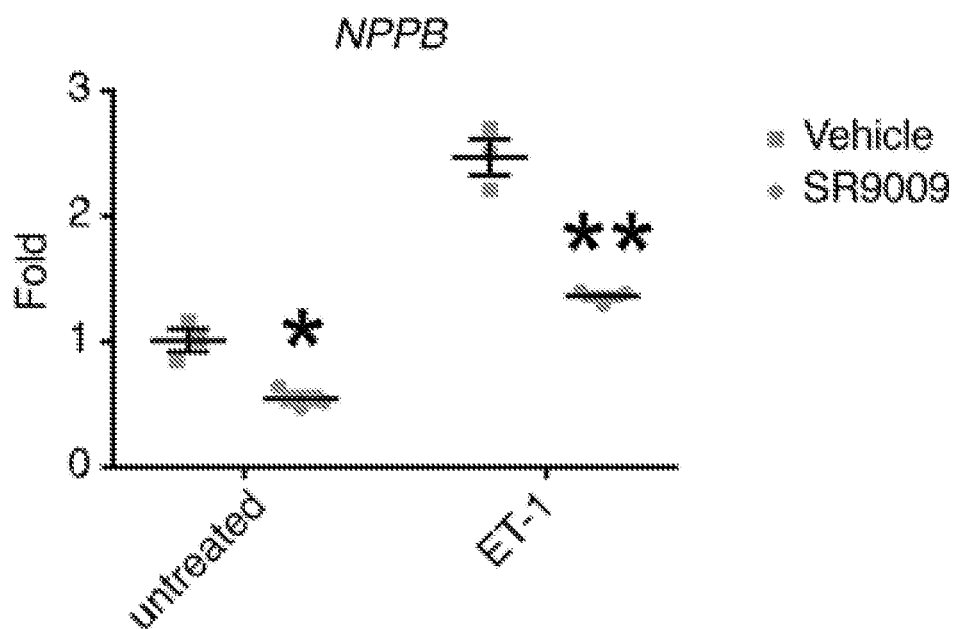
Fig. 5

COMPOSITIONS AND METHODS OF TREATING CARDIAC HYPERTROPHY AND HEART FAILURE

RELATED APPLICATION

This application claims priority from U.S. Provisional Application No. 62/457,579, filed Feb. 10, 2017, the subject matter of which is incorporated herein by reference in their entirety.

GOVERNMENT FUNDING

This invention was made with government support under Grant Nos. RO1HL119195 and KO1HL123551, awarded by The National Institutes of Health. The United States government has certain rights to the invention.

BACKGROUND

Cardiac hypertrophy is an adaptive response to pressure or volume stress, mutations of sarcomeric (or other) proteins, or loss of contractile mass from prior infarction. Hypertrophic growth accompanies many forms of heart disease, including ischemic disease, hypertension, congestive heart failure, valvular disease and subsequent cardiac death. In these types of cardiac pathology, pressure overload-induced concentric hypertrophy is believed to have a compensatory function by diminishing wall stress and oxygen consumption. At the same time, ventricular hypertrophy is associated with significantly increased risk of heart failure and malignant arrhythmia.

REV-ERBα, also known as NR1D1 (nuclear receptor subfamily 1, group D, member 1) is a transcriptional repressor. REV-ERBα is highly expressed in the liver, skeletal muscle, adipose tissue, and the brain, in mammals, participating in the development and circadian regulation of these tissues. REV-ERBα regulates gene transcription by directly binding to target response elements (RevREs), comprises an A/T-rich flank followed by AGGTCA.

SUMMARY

Embodiments described herein relate to compositions and methods for use in the prevention and treatment of cardiac hypertrophy and heart failure. It was found that pharmacological activation of REV-ERBα selectively suppresses aberrant pathologic gene expression and prevents cardiomyocyte hypertrophy. In vivo, REV-ERBα activation prevents development of cardiac hypertrophy, reduces fibrosis, and halts progression of advanced heart failure. Accordingly, in some embodiments a method of treating and/or preventing cardiac hypertrophy and/or heart failure in a subject in need thereof includes administering to the subject a therapeutically effective amount of a REV-ERBα agonist.

In some embodiments, the REV-ERBα agonist is selected from the group consisting of 1,1-Dimethylethyl N-[(4-chlorophenyl)methyl]-N-[(5-nitro-2-thienyl)methyl])glycinate (SR6452); N-Benzyl-N-(4-chlorobenzyl)-1-(5-nitrothiophen-2-yl)methanamine; N-Benzyl-N-(3,4-dichlorobenzyl)-1-(5-nitrothiophen-2-yl)methanamine; 2-((4-chlorobenzyl)((5-nitrothiophen-2-yl)methyl)amino)-N,N-dimethylacetamide, SR9009, SR9011 and pharmaceutically acceptable salts thereof.

BRIEF DESCRIPTION OF THE DRAWINGS

FIGS. 1(A-D) illustrate an image and plots showing REV-ERB agonist prevented the phenylephrine-induced (PE-induced) cardiomyocyte hypertrophy through transcriptional repression of the fetal gene program. (A-C) Neonatal rat ventricular myocytes (NRVMs) were pretreated with vehicle or SR9009 for 24 hours and then treated with PE for 48 hours. (A) Immunofluorescent staining with α-actinin (green). Scale bar: 30 μM. (B) Quantification of cell size. *P=0.02, n=42-114. (C) qPCR of Nppa and Nppb. *P=0.00009 (Nppa), *P=0.00007 (Nppb), n=3. (D) NRVMs were pretreated with vehicle or GSK4112 for 24 hours and then treated with PE for 48 hours. qPCR of Nppa and Nppb. *P=0.00001 (Nppa), *P=0.0003 (Nppb), n=3. Statistical differences were determined by 2-tailed Student's t test. Data are presented as mean±SEM. Multiple comparison is corrected for by using Holm-Sidak method, with α=0.05.

FIGS. 2(A-D) illustrate plots showing REV-ERB agonist ameliorate cardiac dysfunction in pressure-overload models. Six-week followup of 27-gauge TAC performed on 8-week-old mice, vehicle, or SR9009, which were given daily starting 1 day after surgery. n=5. (A) Ejection fraction (EF), *P<0.05. (B) Fraction shortening (FS), *P<0.05. (C) Left ventricle internal diameter end diastole. (D) Left ventricle internal diameter end systole. *P<0.05. Statistical differences were determined by 2-tailed Student's t test. Data are presented as mean±SEM. Multiple comparison is corrected for by using Holm-Sidak method, with α=0.05.

FIGS. 3(A-I) illustrate images and plots showing REV-ERB agonist ameliorate cardiac hypertrophy in pressure overload models. Six-week followup of 27-gauge TAC was performed on 8-weekold mice, vehicle, or SR9009, which were given daily starting one day after surgery. n=5. (A) Left ventricle mass, corrected, *P<0.05. (B) Heart weight normalized to tibia length, *P<0.05. (C) Representative pictures of vehicle- and SR9009-treated hearts harvested at 6 weeks. Scale bar: 5 mm. (D) Wheat germ agglutinin staining. Scale bar: 30 μM. (E) Quantified muscle fiber size in arbitrary units, *P<0.05. 41. (F) Fibrosis stained with Gomori Trichrome stain, representative pictures. Vehicle, left column and middle column. SR9009, right column. Scale bar: 400 μM. (G) Quantification of fibrotic area. (H) TUNEL staining, representative picture. Scale bar: 20 μM. (I) Quantification of TUNEL signal per section. Statistical differences were determined by 2-tailed Student's t test. Data are presented as mean±SEM. Multiple comparison is corrected for by using Holm-Sidak method, with α=0.05.

FIGS. 4(A-B) illustrate a schematic of an experimental design of a twenty-eight-gauge TAC with 11-week followup (B) a graph showing ejection fraction, *P=0.01. Statistical differences were determined by 2-tailed Student's t test. Data are presented as mean±SEM. Multiple comparison is not corrected for. n=5.

FIG. 5 illustrates a plot showing a REV-ERB agonist prevented the endothelin-1-induced (ET-1-induced) hypertrophy in human induced pluripotent stem cell-differentiated cardiomyocytes (iPS-CM). iPS-CM were pretreated with vehicle or SR9009 for 24 hours and then treated with ET-1 for 48 hours. qPCR of Nppb. *P=0.01 (untreated), **P=0.003 (ET-1), n=3. Statistical differences were determined by 2-tailed Student's t test. Data are presented as mean±SEM. Multiple comparison is corrected for by using Holm-Sidak method, with α=0.05.

DETAILED DESCRIPTION OF THE INVENTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

The terms "prevent," "preventing," or "prevention" are art-recognized and include precluding, delaying, averting, obviating, forestalling; stopping, or hindering the onset, incidence, severity, or recurrence of a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. In another aspect, the subject is a prematurely born mammal treated with prolonged supplemental oxygen. A patient refers to a subject afflicted with a disease or disorder.

The terms "prophylactic" or "therapeutic" treatment is art-recognized and includes administration to the host of one or more of the therapeutic compositions described herein. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

As used herein, the term "cardiac hypertrophy" is used in its ordinary meaning as understood by the medical community and is often associated with increased risk of morbidity and mortality. It generally refers to the process in which adult cardiac myocytes respond to stress through hypertrophic growth. Such growth is characterized by cell size increases without cell division or proliferation, assembling of additional sarcomeres within the cell to maximize force generation, and an activation of a fetal cardiac gene program.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. The terms "heart failure," "manifestations of heart failure," "symptoms of heart failure," and the like are used broadly to encompass all of the sequelae associated with heart failure, such as shortness of breath, pitting edema, an enlarged tender liver, engorged neck veins, pulmonary rales and the like including laboratory findings associated with heart failure.

Embodiments described herein relate to compositions and methods for use in the prevention and treatment of cardiac hypertrophy, heart failure, and/or related pathologies. Pathologies related to cardiac hypertrophy and heart failure include ischemic heart disease, hypertension, cardiac fibrosis, valvular disease and additional cardiovascular diseases, such as restrictive cardiomyopathies, valvuloseptal disorders, cardiac dilation and genetic syndromes of dysfunctional heart action.

It was found that pharmacological activation of REV-ERBα selectively suppresses aberrant pathologic gene expression and prevents cardiomyocyte hypertrophy. In vivo, REV-ERBα activation prevents development of cardiac hypertrophy, reduces fibrosis, and halts progression of advanced heart failure. Accordingly, a method of treating, preventing, reversing, ameliorating and/or delaying cardiac hypertrophy, heart failure, and/or related pathologies in a subject having, suspected of having, or at risk of such cardiac hypertrophy, heart failure, and/or related pathologies includes administering to the subject in need thereof a therapeutically effective amount of a REV-ERBα agonist. In some embodiments, the REV-ERBα agonist can be administered at an amount effective to upregulate at least one of REV-ERBα expression, activity, and subcellular localization and/or reduce cardiac hypertrophy, cardiomyocyte death, and/or cardiac fibrosis.

The REV-ERBα agonist can include any agent that either directly or indirectly activates REV-ERBα and that can facilitate REV-ERBα to recruit its corepressor NCoR and repress downstream targets. The REV-ERBα agonist can inhibit cardiomyocyte hypertrophy and cellular stress in a cell-autonomous fashion. The REV-ERBα agonist can include compounds (e.g., small molecules, ligands, proteins, enzymes, antibodies, nucleic acids, etc.) that increase or enhance the activity of REV-ERBα in vivo and/or in vitro. REV-ERBα agonists can also include compounds that exert their effect on REV-ERBα activity via altering expression, via post-translational modifications, or by other means. Agonists of REV-ERBα can comprise molecules which, when bound to REV-ERBα, increase or prolong the activity of REV-ERBα (e.g., increase the nuclear localization and/or nuclear activity of REV-ERBα). Agonists of REV-ERBα according to certain embodiments can include proteins, nucleic acids, carbohydrates, small molecules, or any other molecules which activate REV-ERBα.

In some embodiments, the REV-ERBα agonist can directly upregulate REV-ERBα activity or expression in cardiac cells of a subject. In certain embodiments, the REV-ERBα agonist can include a synthetic ligand (e.g., small molecule) that upregulates REV-ERBα activity or expression. For instance, in certain embodiments, the REV-ERBα agonist can include a synthetic ligand for REV- ERBα. Modulators of REV-ERBα agonist activity and/or expression have been disclosed, e.g., in WO 2013/033310, the contents of which are incorporated herein by reference. Additional REV-ERBα agonists can be identified by screening potential compounds, e.g., as described in Grant et al. (2010), ACS Chem. Biol. 5(10):925-32, the contents of which are incorporated herein by reference. Such potential compounds can include, for example, variants of any REV-ERBα agonist compound specifically disclosed herein.

Examples of synthetic agonists for REV-ERBα include 1,1-Dimethylethyl N-[(4-chlorophenyl)methyl]-N-[(5-nitro-2-thienyl)methyl])glycinate (GSK4112), N-Benzyl-N-(4-chlorobenzyl)-1-(5-nitrothiophen-2-yl)methanamine; N-Benzyl-N-(3,4-dichlorobenzyl)-1-(5-nitrothiophen-2-yl) methanamine, 2-((4-chlorobenzyl)((5-nitrothiophen-2-yl)methyl)amino)-N,N-dimethylacetamide; or combinations thereof. Other examples of synthetic agonists for REV-ERBα include SR9009, SR9011, GSK2945, GSK0999, GSK5072, and/or GS2667, which are described in WO 2013/033310 and are structurally related to the foregoing synthetic agonists. In specific embodiments, the REV-ERBα agonist is SR9009.

Certain embodiments utilize the administration of synthetic REV-ERBα agonist 1,1-Dimethylethyl-N-[(4-chlorophenyl)methyl]-N-[(5-nitro-2-thienyl)methyl])glycinate ($EC_{50}$=250 nM) or salt thereof, which is known as SR6452 or GSK4112 and is commercially available from Sigma Aldrich (USA). 1,1-Dimethylethyl-N-[(4-chlorophenyl) methyl]-N-[(5-nitro-2-thienyl)methyl])glycinate will hereinafter be referred to as "SR6452". REV-ERBα agonist SR6452 enhances recruitment of nuclear receptor co-repressor (NCoR) peptide to REV-ERBα. The structure of SR6452 is as follows:

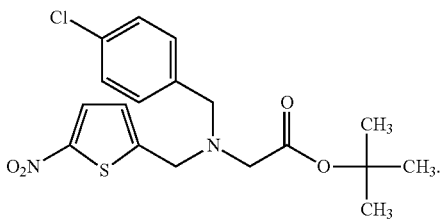 [SMILES: CC(C)(C)OC(=O)CN(Cc1ccc(Cl)cc1)Cc1ccc([N+](=O)[O-])s1]

In certain embodiments, the REV-ERBα agonist can include N-Benzyl-N-(4-chlorobenzyl)-1-(5-nitrothiophen-2-yl)methanamine. The structure of N-Benzyl-N-(4-chlorobenzyl)-1-(5-nitrothiophen-2-yl)methanamine is as follows:

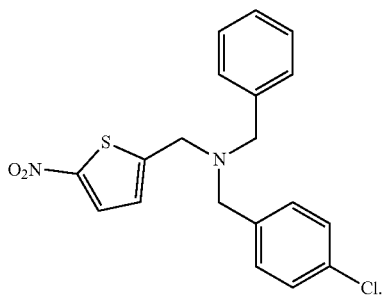 [SMILES: O=[N+]([O-])c1ccc(CN(Cc2ccccc2)Cc2ccc(Cl)cc2)s1]

In certain embodiments, the REV-ERBα agonist can include N-Benzyl-N-(3,4-dichlorobenzyl)-1-(5-nitrothiophen-2-yl)methanamine. The structure of N-Benzyl-N-(3,4-dichlorobenzyl)-1-(5-nitrothiophen-2-yl)methanamine is as follows:

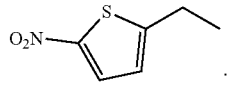

In certain embodiments, the REV-ERBα agonist can include 2-((4-chlorobenzyl)((5-nitrothiophen-2-yl)methyl) amino)-N,N-dimethylacetamide. The structure of 2-((4-chlorobenzyl)((5-nitrothiophen-2-yl)methyl)amino)-N,N-dimethylacetamide is as follows:

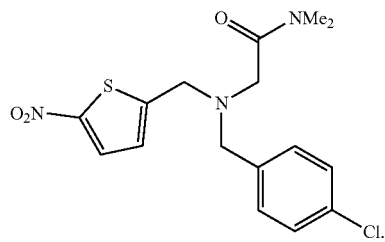 [SMILES: CN(C)C(=O)CN(Cc1ccc(Cl)cc1)Cc1ccc([N+](=O)[O-])s1]

In some embodiments, the REV-ERBα agonist is a 6-substituted [1,2,4]triazolo[4,3-b]pyridazine, such as compounds of general formula (I) described in U.S. Patent Application Publication No. 2017/0296548A1, which is incorporated by reference in its entirety In certain embodiments, the REV-ERBα agonist is a compound related to SR6452, such as SR9009 or SR9011. See, e.g., WO 2013/033310.

In other embodiments, the REV-ERBα agonist can include a natural molecule (e.g., Heme modulators). For instance, a natural REV-ERBα agonist can include enzymes, antibodies, proteins, nucleic acids, carbohydrates, small molecules, or combination thereof including upstream regulators (both known such as glycogen synthase kinase 3 (GSK3) and/or novel).

To improve efficacy and/or reduce side effects, the REV-ERBα agonist can be linked to another moiety that functions as a carrier and/or targeting moiety. The other moiety can selectively targets cardiac cells. The carrier/targeting moiety can, in some embodiments, increase the serum half-life of the REV-ERBα agonist. In other embodiments, the carrier/targeting moiety can increase the serum half-life of the REV-ERBα agonist and selectively targets cardiac cells.

As noted previously, REV-ERBα agonist according to certain embodiments can indirectly modulate REV-ERBα activity or expression. In such embodiments, a REV-ERBα agonist can target or interact with a component of the cardiac cells upstream to REV-ERBα expression or a component that regulates nuclear transport of REV-ERBα. This component, for instance, can then function to modulate REV-ERBα expression or activity. Accordingly, the REV-ERBα agonist effectively modulates REV-ERBα activity or expression indirectly through interaction with the upstream component of the cardiac cell that subsequently affects the activity or expression of REV-ERBα due to the initial interaction with the REV-ERBα agonist. In certain such embodiments, the REV-ERBα agonist can comprise enzymes, antibodies, proteins, nucleic acids, carbohydrates, small molecules, or combinations thereof. The component of the cardiac cell upstream to REV-ERBα expression can comprise, for example, an enzyme, antibody, protein, nucleic acid, carbohydrate, or combinations thereof including upstream regulators (known regulators, such as GSK3, and/or novel regulators).

In some embodiments, a therapeutically effective amount of a REV-ERBα agonist can include an amount sufficient to achieve its intended purpose. More specifically, a therapeutically effective amount can include an amount effective to prevent development of cellular hypertrophy or alleviate the existing symptoms in the subject being treated. A therapeutically effective amount can vary based on a range of factors (e.g., route of administration, patient's age, patient's weight, severity of disorder, etc.) and determination thereof is well within the capability of those skilled in the art.

For instance, a therapeutically effective amount of a REV-ERBα agonist can be estimated initially from cell culture assays. For example, a dose can be formulated in animal models to achieve a circulating concentration range that includes the $IC_{50}$ (the dose where 50% of the cells show the desired effects) as determined in cell culture. Such information can be used to more accurately determine useful doses in mammals (e.g., humans).

A therapeutically effective amount of a REV-ERBα agonist can also refer to that amount of the compound that results in amelioration of symptoms or a prolongation of survival in a patient. Toxicity and therapeutic efficacy of a REV-ERBα agonist can be determined by standard pharmaceutical procedures in cell cultures or experimental animals (e.g., for determining the LD50—the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds, which exhibit high therapeutic indices are preferred. The data obtained from these cell culture assays and animal studies can be used in formulating a range of dosages or amounts for use in mammals (e.g., humans). The dosage or amount of a REV-ERBα agonist preferably lies within a range of circulating concentrations that include the ED50 with little or no toxicity. The dosage or amount may vary within this range depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain the desired effects.

In cases of local administration or selective uptake, the effective local concentration of the REV-ERBα agonist may not be related to plasma concentration.

The amount of REV-ERBα agonist-containing composition administered can, of course, be dependent upon several factors including the subject being treated, on the subject's weight, the severity of the affliction, the manner of administration and the judgment of the prescribing physician.

In certain embodiments, a REV-ERBα agonist can be administered to a mammal having, suspected of having, or at risk of cardiac hypertrophy, heart failure, and/or related pathologies at an amount sufficient to enhance REV-ERBα agonist expression, activity, and/or subcellular location. In accordance with certain embodiments, REV-ERBα agonist expression and/or activity can be enhanced or increased by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, REV-ERBα agonist expression and/or activity can be enhanced or increased from at least any of the following: 1%, 5%, 10%, 15%, 20%, 25%, 30%, 35%, 40%, 45%, 50%, 55%, 60%, 65%, 70%, 75%, 80%, 85%, 90%, 95%, and/or at most about any of the following 5%, 10%, 15%, 20%, 25%, 30%, 35%, 40%, 45%, 50%, 55%, 60%, 65%, 70%, 75%, 80%, 85%, 90%, 95%, 100% (e.g., 5-100%, 10-90%, 20-80%, etc.). In other embodiments, REV-ERBα agonist subcellular localization can be enhanced or increased (e.g., shifted to the nucleus) by at least 1%, 5%, 10%, 15%, 20%, 25%, 30%, 35%, 40%, 45%, 50%, 55%, 60%, 65%, 70%, 75%, 80%, 85%, 90%, 95%, or more. For instance, REV-ERBα agonist subcellular localization can be enhanced or increased (e.g., shifted to the nucleus) such that the amount of REV-ERBα in a particular location (e.g., the nucleus) is from at least any of the following: 30%, 35%, 40%, 45%, 50%, 55%, 60%, 65%, 70%, 75%, 80%, 85%, 90%, 95%, to at most about any of the following 80%, 85%, 90%, 95%, 100% (e.g., 30-100%, 40-90%, 50-80%, etc.).

In certain embodiments, the methods can include the administration of a therapeutically effective amount of a REV-ERBα agonist, in which the amount of the REV-ERBα agonist comprises an amount effective to halt cardiac cell hypertrophy, preferably concomitantly with modulation of REV-ERBα expression, activity, and/or subcellular location. For instance, the rate at which hypertrophic cardiomyocyte growth can begin to reduce until no noticeable further growth is realized. In this regard, these embodiments can provide a means to effectively impede or stop the further progression or severity of cardiac hypertrophy and related pathologies.

In some embodiments, the methods can include the administration of a therapeutically effective amount of a REV-ERBα agonist, in which the amount of the REV-ERBα agonist comprises an amount sufficient to halt and/or reduce cardiac fibrosis, preferably concomitantly with an upregulation or overexpression of REV-ERBα. In such embodiments, the degree of fibrosis can be reduced to beneficially reduce the consequences associated with intracardiac fibrosis such as the contractile function of the cardiac tissue.

In certain embodiments, the subject (e.g., human) being treated has been diagnosed as having cardiac hypertrophy. In other embodiments, however, the subject (e.g., human) being treated may not technically have cardiac hypertrophy but may be exhibiting symptoms similar to or associated with cardiac hypertrophy. In certain embodiments, the subject (e.g., human) being treated may be identified as being at risk of developing cardiac hypertrophy, cardiac hypertrophy associated cardiovascular disease and/or heart failure in view of diagnosis of conditions known to ultimately lead to development of cardiovascular disease. In such embodiments, the administration of a REV-ERBα agonist n can beneficially facilitate or prevent development of cardiac hypertrophy, cardiac hypertrophy associated cardiovascular disease and/or heart failure.

In some embodiments, the REV-ERBα agonist can provided in a pharmaceutical composition with a wide variety of pharmaceutically acceptable carriers or excipients. The particular carriers or excipients can be varied depending on various factors including route of administration, presence or absence of a carrier/targeting moiety, and desired delivery system (e.g., sustained release, timed-released, immediate release, selective release, etc.). For example, the composition can be made to suit the desired mode of administration. Pharmaceutically acceptable carriers can be determined, in part, by the particular composition being administered, as well as by the particular method used to administer the composition. Accordingly, there is a wide variety of suitable formulation recipes of pharmaceutical compositions containing one or more REV-ERBα agonists. For example, the pharmaceutical carrier may comprise a virus, a liposome (e.g., cationic lipids mixed with a REV-ERBα agonist to form liposomes carrying the REMA), or a polymer (e.g., cationic polymers such as DEAE-dextran or polyethylenimine in which the REV-ERBα agonist complexes with the polycation and the complex is taken up by the cell via endocytosis).

The administration of a pharmaceutical composition that includes a REV-ERBα agonist may be carried out by known methods, wherein a desired molecule is introduced into a desired target cell in vitro or in vivo. In general, methods of administering small molecules, nucleic acids, enzymes and proteins are well known in the art. REV-ERBα agonist compositions in accordance with some embodiments can be administered by a number of routes including, but not limited to: oral, intravenous, intraperitoneal, intraarterial, intramuscular, transdermal, subcutaneous, topical, sublingual, or rectal means. Alternatively, the REV-ERBα agonist can be administered using a cellular vehicle, such as cells "loaded" with the REV-ERBα agonist ex vivo.

Administration of the compositions described herein may be accomplished by any acceptable method which allows a REV-ERBα agonist to reach its target. Any acceptable method known to one of ordinary skill in the art may be used to administer a composition to the subject. The administration may be localized (i.e., to a particular region, physiological system, tissue, organ, or cell type) or systemic, depending on the condition being treated. In certain embodiments, the targeted tissue comprises a cardiomyocyte.

Injections can be, for example, intravenous, intradermal, subcutaneous, intramuscular, or intraperitoneal. In certain embodiments, the injections can be given at multiple locations if desired. In certain embodiments, the compositions can be delivered by implantation. Implantation can include inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. In certain embodiments, the compositions can be delivered orally or sublingually. In certain embodiments, the compositions can be delivered by inhalation. Inhalation can include administering the composition with an aerosol in an inhaler, either alone or attached to a carrier that can be absorbed. For systemic administration, it may be preferred that the composition is encapsulated in liposomes.

In some embodiments, the REV-ERBα agonist delivery systems can be provided in a manner which enables tissue-specific uptake of the REV-ERBα agonist. Techniques include using tissue or organ localizing devices, such asstents having drug delivery capability and configured as expansive devices or stent grafts.

In some embodiments, a nucleic acid encoding a REV-ERBα agonist can be provided in a vector. Such vectors can include a sequence encoding a particular REV-ERBα agonist of choice and in vivo expression elements. Vectors can include, but are not limited to, plasmids, cosmids, phagemids, viruses, other vehicles derived from viral or bacterial sources that have been manipulated by the insertion or incorporation of the nucleic acid sequences for producing the desired REV-ERBα agonist, and free nucleic acid fragments which can be attached to these nucleic acid sequences. Viral and retroviral vectors are a preferred type of vector according to certain embodiments and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which nonessential genes have been replaced with the nucleic acid sequence of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Genetically altered retroviral expression vectors have general utility for the high-efficiency transduction of nucleic acids in vivo.

Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

In certain embodiments, a therapeutically effective amount of one or more REV-ERBα agonists can be delivered to a mammal via a nanoparticle-based drug delivery system. For instance, nanoparticles used as carriers for REV-ERBα agonists can provide the benefits of high stability, high carrier capacity, feasibility of incorporation of both hydrophilic and hydrophobic substances, and feasibility of variable routes of administration, including oral application and inhalation. In certain embodiments, the nanoparticles can also be designed to allow controlled (sustained) release of the REV-ERBα agonists from the matrix. The aforementioned properties of nanoparticles, according to certain embodiments of the present invention, can provide improvement of bioavailability and/or reduction of the dosing frequency. Nanoparticles for the purpose of REV-ERBα agonist delivery can be defined as submicron (<1 μm) colloidal particles. The colloidal particles can include monolithic nanoparticles (nanospheres) in which the REV-ERBα agonist is adsorbed, dissolved, or dispersed throughout the matrix and nanocapsules in which the REV-ERBα agonist is confined to an aqueous or oily core surrounded by a shell-like wall. Alternatively, the REV-ERBα agonists can be covalently attached to the surface or into the matrix. Nanoparticles, according to certain embodiments of the present invention, can be made from biocompatible and biodegradable materials such as polymers, either natural (e.g., gelatin, albumin) or synthetic (e.g., polylactides, polyalkylcyanoacrylates), or solid lipids. In the body of the mammal being treated, the REV-ERBα agonists loaded in nanoparticles can be released from the matrix by a variety of mechanisms including, for example, diffusion, swelling, erosion, degradation, or combinations thereof. In one embodiment, the composition comprising one or more REV-ERBα agonists can be perfused directly through the targeted tissue. For example, the composition containing a REV-ERBα agonist can be perfused directly through a body organ, without introducing the REV-ERBα agonist into the body's general circulation, removing them from the organ with effluent blood and transporting the contaminated blood to an extracorporeal circuit where the blood is treated to remove the contamination, and returning the treated blood to the body. In some embodiments, such a process may help prevent undesirable levels of the REV-ERBα agonist from entering the body's general circulation while delivering effective doses to the cardiomyocytes. Methods of perfusing active agents through a body organ, are described in greater detail in U.S. Pat. No. 5,069,662, the contents of which are incorporated by reference in their entirety.

In certain embodiments, the compositions can be delivered using a bioerodible implant by way of diffusion or by degradation of a polymeric matrix. In certain embodiments, the administration of the compositions may be designed so as to result in sequential exposures to the REV-ERBα agonist over a certain time period, for example, hours, days, weeks, months or years. This may be accomplished, for example, by repeated administrations or by a sustained or controlled release delivery system in which a REV-ERBα agonist is delivered over a prolonged period without repeated administrations. Administration of the compositions using such a delivery system may be, for example, by oral dosage forms (e.g., tablet, capsule, etc.), bolus injections, transdermal patches or subcutaneous implants. Maintaining a substantially constant concentration of the REV-ERBα agonist may be preferred in some cases.

Other delivery systems include, but are not limited to, time-release, delayed release, sustained release, or controlled release delivery systems (e.g., tablets, capsules, etc.). Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these.

Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which a synthetic compound (e.g., SR6452, SR9009, SR9011) is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The compositions may be as, for example, microspheres, hydrogels, polymeric reservoirs, cholesterol matrices, or polymeric systems. In certain embodiments, the system may allow sustained or controlled release of the composition to occur, for example, through control of the diffusion or erosion/degradation rate of the formulation containing the REV-ERBα agonist. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g., by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose can be determined by the efficacy of the particular formulation, and the activity, stability or serum half-life of the REV-ERBα agonist employed and the condition of the patient, as well as the body weight or surface area of the patient to be treated. The size of the dose can also be determined by the existence, nature, and extent of any adverse side-effects that accompany the administration of a particular composition in a particular patient.

Optimal precision in achieving concentrations of the therapeutic regimen (e.g., a pharmaceutical composition comprising one or more REV-ERBα agonists) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. Generally, the pharmaceutical compositions of the present invention may be administered in a manner that maximizes efficacy and minimizes toxicity.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.01 µg-30 mg, about 0.01 µg-20 mg or about 0.01-10 mg per day to adults (at about 60 kg). In the case of other animals, the dose calculated for 60 kg may be administered as well.

Doses of a pharmaceutical composition of the present invention can optionally include 0.0001 µg to 1,000 mg/kg/administration, or 0.001 µg to 100.0 mg/kg/administration, from 0.01 µg to 10 mg/kg/administration, from 0.1 µg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 m/ml serum concentration per single or multiple administration or any range, value or fraction thereof.

As a non-limiting example, treatment of humans or animals can be provided as a onetime or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days. The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

Therapeutic compositions that include one or more REV-ERBα agonists can optionally be tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the REV-ERBα agonist at various concentrations, e.g., as applied to the mass and overall health of the patient. Administration can be accomplished via single or divided doses.

In some embodiments, the pharmaceutical compositions (e.g., the REV-ERBα agonist) can be combined with one or more therapeutic agents. In particular, the compositions described herein and other therapeutic agents can be administered simultaneously or sequentially by the same or different routes of administration. The determination of the identity and amount of therapeutic agent(s) for use in the methods described herein can be readily made by ordinarily skilled medical practitioners using standard techniques known in the art. In specific embodiments, a REV-ERBα agonist of the present invention can be administered in combination with an effective amount of a therapeutic agent that treats cardiac hypertrophy and/or any heart disease associated with cardiac hypertrophy.

Therapeutic agents include, but are not limited to, beta blockers, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin type 2 antagonists and cytokine blockers/inhibitors, and HDAC inhibitors.

More specifically, a REV-ERBα agonist may be combined with another therapeutic agent including, but not limited to, an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In specific embodiments, a REV-ERBα agonist may be combined with an antihyperlipoproteinemic agent including aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof, acifran, azacosterol, benfluorex, β-benzalbutyramide, carnitine, chondroitin sulfate, clomestrone, detaxtran, dextran sulfate sodium, eritadenine, furazabol, meglutol, melinamide, mytatrienediol, ornithine, γ-oryzanol, pantethine, pentaerythritol tetraacetate, phenylbutyramide, pirozadil, probucol (lorelco), β-sitosterol, sultosilic acid-piperazine salt, tiadenol, triparanol and xenbucin.

A REV-ERBα agonist may be combined with an antiarteriosclerotic agent such as pyridinol carbamate. In other embodiments, a REV-ERBα agonist may be combined with an antithrombotic/fibrinolytic agent including, but not limited to anticoagulants (acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin); anticoagulant antagonists, antiplatelet agents (aspirin, a dextran, dipyridamole (persantin), heparin, sulfinpyranone (anturane) and ticlopidine (ticlid)); thrombolytic agents (tissue plaminogen activator (activase), plasmin, pro-urokinase, urokinase (abbokinase) streptokinase (streptase), anistreplase/APSAC (eminase)); thrombolytic agent antagonists or combinations thereof).

In other embodiments, a REV-ERBα agonist may be combined with a blood coagulant including, but not limited to, thrombolytic agent antagonists (amiocaproic acid (amicar) and tranexamic acid (amstat); antithrombotics (anagrelide, argatroban, cilstazol, daltroban, defibrotide, enoxaparin, fraxiparine, indobufen, lamoparan, ozagrel, picotamide, plafibride, tedelparin, ticlopidine and triflusal); and anticoagulant antagonists (protamine and vitamin K1).

Alternatively, a REV-ERBα may be combined with an antiarrhythmic agent including, but not limited to, Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents. Non-limiting examples of sodium channel blockers include Class IA (disppyramide (norpace), procainamide (pronestyl) and quinidine (quinidex)); Class IB (lidocaine (xylocalne), tocamide (tonocard) and mexiletine (mexitil)); and Class IC antiarrhythmic agents, (encamide (enkaid) and fiecamide (tambocor)).

Non-limiting examples of a beta blocker (also known as a β-adrenergic blocker, a β-adrenergic antagonist or a Class II antiarrhythmic agent) include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfmalol, talinolol, tertatolol, timolol, toliprolol and xibinolol.

In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol. Non-limiting examples of an agent that prolongs repolarization, also known as a Class III antiarrhythmic agent, include amiodarone (cordarone) and sotalol (betapace).

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

In other embodiments, a REV-ERBα agonist may be combined with an antihypertensive agent including, but not limited to, alpha/beta blockers (labetalol (normodyne, trandate)), alpha blockers, anti-angiotensin II agents, sympatholytics, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

Non-limiting examples of anti-angiotension II agents include angiotensin converting enzyme inhibitors and angiotension II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan. Non-limiting examples of a sympatholytic include a centrally acting sympatholytic or a peripherally acting sympatholytic. Non-limiting examples of a centrally acting sympatholytic, also known as a central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or an al-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alphal-adrenergic blocker include prazosin (minipress), doxazocin (cardura) and terazosin (hytrin).

In certain embodiments, an antihypertensive agent may comprise a vasodilator (e.g., a cerebral vasodilator, a coronary vasodilator or a peripheral vasodilator). In particular embodiments, a vasodilator comprises a coronary vasodilator including, but not limited to, amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(P-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil. In certain aspects, an antihypertensive may comprise an arylethanolamine derivative (amosulalol, bufuralol, dilevalol, labetalol, pronethalol, sotalol and sulfmalol); a benzothiadiazine derivative (althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethiazide, methyclothiazide, meticrane, metolazone, paraflutizide, polythizide, tetrachlormethiazide and trichlonnethiazide); a N-carboxyalkyl(peptide/lactam) derivative (alacepril, captopril, cilazapril, delapril, enalapril, enalaprilat, fosinopril, lisinopril, moveltipril, perindopril, quinapril and ramipril); a dihydropyridine derivative (amlodipine, felodipine, isradipine, nicardipine, nifedipine, nilvadipine, nisoldipine and nitrendipine); a guanidine derivative (bethanidine, debrisoquin, guanabenz, guanacline, guanadrel, guanazodine, guanethidine, guanfacine, guanochlor, guanoxabenz and guanoxan); a hydrazines/phthalazine (budralazine, cadralazine, dihydralazine, endralazine, hydracarbazine, hydralazine, pheniprazine, pildralazine and todralazine); an imidazole derivative (clonidine, lofexidine, phentolamine, tiamenidine and tolonidine); a quaternary ammonium compound (azamethonium bromide, chlorisondamine chloride, hexamethonium, pentacynium bis(methylsulfate), pentamethonium bromide, pentolinium tartrate, phenactropinium chloride and trimethidinium methosulfate); a reserpine derivative (bietaserpine, deserpidine, rescinnamine, reserpine and syrosingopine); or a sulfonamide derivative (ambuside, clopamide, faro semide, indapamide, quinethazone, tripamide and xipamide).

In other embodiments, a REV-ERBα agonist may be combined with a vasopressor. Vasopressors generally are used to increase blood pressure during shock, which may occur during a surgical procedure. Non-limiting examples of a vasopressor, also known as an antihypotensive include amezinium methyl sulfate, angiotensin amide, dimetofrine, dopamine, etifelmin, etilefrin, gepefrine, metaraminol, midodrine, norepinephrine, pholedrine and synephrine.

A REV-ERBα agonist may be combined with treatment agents for congestive heart failure including, but not limited to, anti-angiotension II agents, afterload-preload reduction treatment (hydralazine (apresoline) and isosorbide dinitrate (isordil, sorbitrate)), diuretics, and inotropic agents.

Non-limiting examples of a diuretic include a thiazide or benzothiadiazine derivative (e.g., althiazide, bendroflumethazide, beizthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythropleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for hypertrophy, vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Alternatively, therapeutic agents that can be administered in combination therapy with one or more REV-ERBα agonists include, but are not limited to, anti-inflammatory, anti-viral, anti-fungal, anti-mycobacterial, antibiotic, amoebicidal, trichomonocidal, analgesic, anti-neoplastic, antihypertensives, anti-microbial and/or steroid drugs, to treat cardiac hypertrophy and/or any heart disease associated with cardiac hypertrophy. In some embodiments, patients are treated with a REV-ERBα agonist in combination with one or more of the following; β-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), pro tease inhibitors, saquinavir (Invirase™, Fortovase™), ritonavir (Norvir™), nelfmavir (Viracept™), efavirenz (Sustiva™), abacavir (Ziagent™), amprenavir (Agenerase™) indinavir (Crixivan™), ganciclovir, AzDU, delavirdine (Kescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparagyinase and combinations foregoing.

In another aspect, the REV-ERBα agonists may be combined with other therapeutic agents including, but not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal antiinflammatory drugs (e.g., aspirin, ibuprofen, diclofenac, and COX-2 inhibitors), and leukotreine antagonists (e.g., montelukast, methyl xanthines, zafirlukast, and zileuton), β2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), other anti-viral agents, and antibiotics (e.g., dactinomycin (formerly actinomycin), bleomycin, erythomycin, penicillin, mithramycin, and anthramycin (AMC)).

In various embodiments, a REV-ERBα agonist in combination with a second therapeutic agent may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patient visit.

In certain embodiments, a REV-ERBα agonist and one or more other therapies are cyclically administered. Cycling therapy involves the administration of a first therapy (e.g., a REV-ERBα agonist) for a period of time, followed by the administration of a second therapy (e.g., a second REV-ERBα agonist or another therapeutic agent) for a period of time, optionally, followed by the administration of a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

The dosages of a pharmaceutical composition disclosed herein may be adjusted when combined to achieve desired effects. On the other hand, dosages of the pharmaceutical composition and various therapeutic agents may be independently optimized and combined to achieve a synergistic result wherein the pathology is reduced more than it would be if either were used alone.

The following example is included to demonstrate different embodiments of the invention. It should be appreciated by those of skill in the art that the techniques disclosed in the example, which follow represent techniques discovered by the inventors to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example

We set out to determine whether REV-ERBα functions in hypertrophic growth of cardiomyocytes that accompanies many forms of heart disease and whether a REV-ERBα modulation is effective in the prevention of cardiomyocyte cellular hypertrophy.

Animals

WT C57BL/6J mice were purchased from the Jackson Laboratory at the age of 7 weeks and allowed to acclimate in the Case Western Reserve University for 2 weeks prior to the experiments described below. Sprague-Dawley rat pups were purchased from the Charles River Laboratories at 2 days of age and sacrificed for NRVMs isolation upon arrival.

Preparation and Administration of SR9009 and GSK41112

SR9009 was synthesized and purified in the laboratory of Thomas Burris (Department of Pharmacology and Physiology, St. Louis University, St. Louis, Mo., USA). For in vitro experiments, SR9009 was dissolved in DMSO and administered at 5 M; GSK4112 (EMD Millipore) was dissolved in DMSO and administered at 10 M using an equal volume of DMSO as control. For in vivo experiments, SR9009 was dissolved in 5% DMSO/10% Cremaphor EL (Sigma-Aldrich, C5135)/85% PBS in a working solution at 10 mg/ml. Micewere injected at a dose of 100 mg/kg/day given i.p. once daily at zeitgeber time 8 (ZT8). The diluent without SR9009 of the same volume was used as control.

TAC

All mice were C57BL/6J littermate males aged 9 weeks at the start of the experiment. Mice were anesthetized with ketamine/xylazine, mechanically ventilated (Harvard apparatus), and subjected to thoracotomy. The aortic arch was constricted between the left and right carotid arteries using a 7.0 silk suture and a 27- or 28-gauge needle as previously described (20). Chemicals were obtained from Sigma-Aldrich.

Echocardiography

For transthoracic echocardiography, mice were anesthetized with 1% inhalational isofluorane and imaged using the Vevo 770 High Resolution Imaging System (Visual Sonics Inc.) and the RMV-707B 30 MHz probe. Measurements were obtained from M-mode sampling, and integrated EKVimages were taken in the LV short axis at the mid-papillary level.

Blood Pressure

Conscious tail-vein systolic blood pressure was measured using the BP2000 Blood Pressure Analysis System (Visitech Systems Inc.) as recommended by the manufacturer. To allow mice to adapt to the apparatus, we performed daily blood pressure measurements for 1 week prior to beginning experiments.

NRVMs and CF Culture

NRVMs and CFs were isolated from the hearts of 2-day-old Sprague-Dawley rat pups (Charles River Laboratories). The cells were differentially preplated for 1.5 hr. The non-attached cells were collected as NRVM and replated with 48 hr exposure to BrdU to suppress nonmyocytes. The attached cells were passaged 2-3 times to obtain CFs. NRVMs were initially plated in growth medium (DMEM supplemented with 10% FBS, 100 U/ml penicillin-streptomycin, and 2 mM L-glutamine) for 48 hr and maintained in serum-free media thereafter (DMEM supplemented with 1% insulin-transferrin-selenium liquid media supplement [Sigma-Aldrich, 13146], 100 U/ml penicillin-streptomycin). For hypertrophic stimulation, NRVM were incubated with SR9009 or GSK4112 versus DMSO for 24 hr, followed by stimulation with PE (100 μM) for the indicated time. CFs were cultured in DMEM supplemented with 10% FBS, 100 U/ml penicillin-streptomycin, and 2 mM L-glutamine and stimulated with TGβ1 (eBioscience).

Human Cardiomyocytes Culture

We purchased human induced pluripotent stem cell-differentiated cardiomyocytes from Cellular Dynamics (iCell). We followed manufacturer's protocol and measured NPPB expression 24 hr after ET-1 (10 nM, Sigma-Aldrich) induction.

Cell Area Measurements

NRVM were plated on glass coverslips in 6-well dishes at a density of 1×105 cells/ml. After treatments, cells were fixed in ice cold methanol, permeabilized with PBST/0.3% Triton X-100, and blocked in PBST/5% horse serum. Primary antibody was anti-α-actinin (Sigma-Aldrich, A7811) at 1:500. Secondary antibody (anti-mouse Alexa 488, Life Technologies) was used at 1:1,000 dilution. Coverslips were mounted on glass slides with mounting media containing DAPI. Quantitation of cardiomyocyte cell surface area was performed on anti-actinin-stained cardiomyocytes using fluorescent microscopy and ImagePro software. Analysis consisted of at least 200 cardiomyocytes in 20-30 fields at 400× magnification. Three independent experiments were performed.

Histological Analysis

Short-axis heart sections from the midventricle were fixed in PBS/4% paraformaldehyde and embedded in paraffin. Fibrosis was visualized using Gomori's Trichrome staining kit (Sigma-Aldrich) with quantification of fibrotic area using ImagePro software. TUNEL staining was performed using the CardioTACS In Situ Apoptosis Detection kit (R&D Systems) according to manufacturer's instructions. Cryopreserved sections were used for myocardial capillary staining, which was performed in frozen LV sections using anti-PECAM-1 antibodies (1:200, BD Pharmingen, MEC13.3). The cardiomyocyte cross-sectional area was determined by staining with WGA Alexa 594 (Life Technologies) and analyzed using ImagePro software.

RNA Purification and Quantitative PCR

For tissue RNA, a 10-20 mg piece of mouse heart at apex was preserved in RNA Later stabilization reagent (Qiagen) followed by mechanical disruption/homogenization in Trizol (Life Technologies) on a TissueLyser (Qiagen) using stainless steel beads (Qiagen). RNA was purified from the aqueous phase using the miRNAeasy kit (Qiagen) following manufacturer's instructions. For cellular samples, total RNA from NRVM was isolated using the High Pure RNA isolation kit (Roche Diagnostics) with on-column DNAase treatment according to manufacturer's directions. Purified RNA was reverse transcribed to complementary DNA using the iScript™ RT Supermix (Bio-Rad) following manufacturer's protocol. qPCR was performed using TaqMan chemistry (Taqman Fast Advanced Master Mix, Applied Biosystems) and labeled probes from the Roche Universal Probe Library System on Applied Biosystems ViiA 7. Relative expression was calculated using the ΔΔCt-method with normalization to Ppib (Cyclophilin-B). Specific primer/probe sequences are available upon request. For RNA-Seq, libraries were prepared using the Illumina TruSeq Stranded Total RNA Sample Preparation kit according to the manufacturer's protocol. Singled-end sequencing (50 bp) was performed on pooled libraries in groups of 3 using an Illumina HiSeq 2500.

RNA-Seq and ChIP-Seq Analyses.

Sequencing reads generated from the Illumina platform were assessed for quality using FastQC. The reads were then trimmed for adapter sequences using TrimGalore. For RNA-Seq, reads that passed quality control were then aligned to rn6 using TopHat (21). The TopHat results were then analyzed for differential expression using Cufflinks to generate the fragments per kilobase of exon per million fragments mapped (FPKM) for each gene (22). Differential genes were identified using a significance cutoff of $q<0.005$ and fold change $>1.5$. These genes were then subjected to further analysis. All original RNA-Seq data were deposited in the NCBI's GEO (GSE98575). For ChIP-Seq, the reads that passed quality control were aligned to mouse genome release mm9 using Burrows-Wheeler Alignment (BWA) (23). Peaks were called using MACS 1.4.2 (24). The default P value for peak detection was used ($1\times10$-5). Further annotation and analysis of the called peaks were performed using HOMER, using default settings. For each immunoprecipitated sample, a matching chromatin input sample was used.

Hierarchical Clustering

The hierarchical relationship for the samples was determined using differentially expressed genes between all pairwise comparison groups. The samples were clustered using Hierarchical-Clustering v6 (Broad Institute) by pairwise average-linkage according to the distance measure using the Pearson correlation coefficient. Heatmaps and dendrograms were generated from the output of the HierarchicalClustering using Java TreeView.

GSEA

Enriched pathways were determined using GSEA v17.6 using GenePattern and the Molecular Signature Database (MSigDB; Broad Institute). The FPKM values from significantly differentially expressed genes ($q<0.005$ and fold change $>1.5$) as determined from the Cufflinks software were normalized for each gene across all samples, and the Z score was used as input for pathway analysis. The gene set used for comparison was the KEGG database, and enrichment significance was determined using 1000 genomes project. Pathways were considered enriched using a significance cutoff FWER $<0.25$.

Gene Ontology Analysis

KEGG analysis were performed using DAVID bioinformatics suite.

Mitochondrial Respiration Studies

The assay was performed using Seahorse (Agilent) and following the manufacturer's published protocol. Isolated mitochondria (0.5 μg; measured by BCA assay) were loaded per assay.

Mitochondrial Genome Quantification

Total DNA was extracted from the hearts or NRVMs using the QIAamp DNA Mini Kit (Qiagen, 51304). Mitochondrial DNA content was assessed by qPCR using primers specific for multiple mitochondrial-encoded genes (int-Cox1, mt-Nd2, int-Nd1, and mt-Nd5) and normalized to nuclear DNA content (a specific locus on mouse chromosome 6) using the ΔΔCt method.

Transmission Electron Microscopy

Small pieces of tissue from the LV free wall were fixed by sequential immersion in triple aldehyde-DMSO, ferrocyanide-reduced osmium tetroxide, and acidified uranyl acetate; dehydrated in ascending concentrations of ethanol; passed through propylene oxide; and embedded in Poly/Bed resin (Polysciences Inc., 21844-1). Thin sections were sequentially stained with acidified uranyl acetate, followed by a modification of Sato's triple lead stain, and examined with a JEOL 1200EX electron microscope.

Results

To start deciphering its function in the heart, we analyzed our previously reported REV-ERBα cistrome in the heart. Similar to previous reports in the liver and macrophages, the top enriched motifs are REV-ERBα's own DNA cognate sites (ROR and Reverb, DR2), followed by tissue-specific factor sites, MEF2a and MEF2c. MEF2a and MEF2c are known drivers of the cardiac hypertrophy gene program, and previous studies show that ectopic expression of MEF2a or MEF2c in the heart leads to dilated cardiomyopathy and HF. They are also the top enriched enhancer motifs that undergo chromatin state switching in a murine cardiac pressure overload model. The colocalization of REV-ERBα to MEF2a and MEF2c suggests that it may specifically repress the aberrantly activated gene program during cardiac hypertrophy and HF driven by MEF2a and MEF2c. SR9009 is a validated synthetic REV-ERB agonist, which facilitates REV-ERBα to recruit its corepressor NCoR and repress downstream targets. We first tested the effect of SR9009 directly in primary cardiomyocytes in vitro. In neonatal rat ventricular myocytes (NRVMs), SR9009 effectively blocked the phenylephrine-induced (PE-induced) cellular hypertrophy and expression of cellular stress markers (FIG. 1, A-C). Further, another independently developed, structurally distinct REV-ERB agonist, GSK4112, also showed a similar result (FIG. 2D). Thus, activation of REV-ERB leads to blockade of cardiomyocyte hypertrophy and cellular stress in a cell-autonomous fashion.

We subsequently focused our study using SR9009 due to its higher efficacy and favorable in vivo pharmacodynamics. To elucidate the molecular mechanisms underlying REV-ERBα effects, we performed RNA-Seq on NRVM at baseline and after PE stimulation (4 hours [hr] and 48 hr) in the presence or absence of SR9009 (SR or Veh were given 24 hr prior to PE). All original RNA-Seq data were deposited in the NCBI's Gene Expression Omnibus (GEO GSE98575). All the genes with pairwise differential expression between SR9009 and vehicle-treated (Veh-treated) groups at each time point were analyzed using Gene Set Enrichment Analysis (GSEA), and the genes in the altered pathways (defined by family-wise error rate [FWER]<0.25) were further analyzed using unsupervised hierarchical clustering. Veh-PE-treated groups showed a shift in gene expression patterns at 4 hr that continued to deviate from the baseline with time. In contrast, the SR-treated groups displayed an expression pattern more similar to the baseline groups, despite the persistent exposure to PE for 48 hr. We then compared the number of differentially expressed genes in each group (vs. Veh-baseline and defined by changes >1.5-fold and q<0.005).

We found that, while the Veh-treated groups have about equal number of genes being up- or downregulated, the SR-treated groups have twice as many genes being downregulated than upregulated, consistent with its role as a transcriptional repressor. Further, as the total number of differential genes continue to increase from 4 hours of vehicle treatment (Veh-4h) to Veh-48h, indicative of the continuation of the hypertrophy process, the SR-48h had significantly fewer differentially expressed genes compared with the early time point SR-4h, suggesting the hypertrophy process was blocked at the transcriptional level. Representative genes with REV-ERBα and MEF2a cooccupancy and transcription repression by SR9009 treatment were shown. Using GSEA, we analyzed the differentially expressed genes between SR9009 and Veh at each time point. Baseline and 4-hr time points were combined, as they showed the same top enriched pathway (hypertrophic cardiomyopathy) when analyzed individually. Veh-treated cells showed an enrichment for cardiomyopathy and contractile pathways at baseline and 4 hr. The activation of hypertrophic pathways at baseline in the Veh-treated group suggests that, under the current culture condition (without PE), there is a low level of spontaneous hypertrophy that is prevented by SR9009 treatment.

Forty-eight hr after PE exposure, the Veh-treated group showed an enrichment for remodeling and inflammation pathways most consistent with the advanced hypertrophic stage, while the SR9009-treated group showed an enrichment of cellular metabolism pathways known to be downregulated in the failing heart. These results suggest that the REV-ERB agonist exerts its effect mainly through gene repression and that the difference between the SR9009 and Veh groups lies in the genes and pathways that are up- or downregulated in the Veh groups and less changed in the SR9009 groups, as Nppa and Nppb show in FIG. 1D.

As a large number of genes involved in the fatty acid oxidation pathway maintained their expression with SR9009 treatment, we investigated the role of PDK4, an important modulator of the pathway. Interestingly, we observed a cooccupation of MEF2A and REV-ERBα on the promoter and an enhancer element at the Pdk4 locus. In addition, PE represses the expression of Pdk4, which is ameliorated by SR9009 treatment, as seen in our RNA-Seq result. PDK4 is likely one of the main targets of REV-ERBα during cardiac metabolic remodeling.

Given the strong effect of SR9009 in blocking the cellular remodeling in response to neurohormonal stress, we next tested the role of REV-ERBα activation in vivo using the classical pressure overload model. We started daily i.p. injection of SR9009 or Veh 1 day after transaortic constriction (TAC, 27 gauge) surgery and monitored cardiac hypertrophy and function by echocardiogram for 6 weeks. The SR9009 dose (10 mg/kg/day) was previously established and displayed no apparent toxicity. We found that, while mice treated with Veh demonstrated a gradual reduction in cardiac function (ejection fraction [EF]=52.8% at 4 weeks and EF=46.9% at 6 weeks), SR9009-treated animals maintained normal cardiac function (EF=61.4% at 4 weeks and EF=60.6% at 6 weeks, P=0.03) (FIG. 2, A-D). The SR9009-treated group also showed significantly less cardiac hypertrophy measured by echocardiogram. The corrected left ventricle mass (LVm) showed a continued increase in the Veh-treated group (LVm=129.6 mg at 4 weeks and LVm=139.2 mg at 6 weeks), which is attenuated in the SR9009-treated group (LVm=111.4 mg at 4 weeks [P=0.01] and LVm=114.8 mg at 6 weeks [P=0.02]). The left ventricle posterior wall thickness (LVPW; diastole [d]) and intraventricular septum thickness (IVS; d) showed similar trends (FIG. 3A). These findings were later confirmed by autopsy performed 6 weeks after TAC by heart weight and muscle fiber size analyses using wheat germ agglutinin staining on cryopreserved sections (FIGS. 3, B-E).

Furthermore, we observed drastically reduced intracardiac fibrosis in the SR9009-treated group. At the end of 6 weeks after TAC, the Veh-treated group showed an intramuscular fibrosis area of 10.3%, while the SR9009-treated groups showed no significant fibrosis, with an intramuscular fibrosis area of 1.1%, P=0.003 (FIGS. 3, F and G). Cell death quantified by TUNEL assay also indicated that there is more cell death in the Veh-treated group (27.8 tunnel positive cells per cross-section of the whole heart) than the SR9009-treated group (13.4 positives per cross-section of the whole heart, P=0.002) (FIGS. 3, H and I).

SR9009 is a drug given systemically and may potentially affect other systems, such as the vascular tone, although pressure overload itself is considered a relatively specific stress directly on the heart. To exclude the possibility that the improved cardiac function and reduced hypertrophy in vivo is associated with improvement in hemodynamics, we measured blood pressure using tail cuff and found there is no difference in mice receiving 4 weeks of Veh (mean arterial pressure [MAP]=106 mmHg) or SR9009 (MAP=115 mmHg, P=0.24). Since there is a substantially improved fibrosis in the SR9009-treated heart, we also investigated if the in vivo protection is directly on cardiomyocytes or through cardiac fibroblasts (CFs).

We found there is no difference in the TGβ1-induced inflammatory response of cultured CFs pretreated with Veh or SR9009. Further, we see no difference in capillary density after 6 weeks of TAC between Veh- and SR9009-treated groups, suggesting there is no secondary benefits through improved angiogenesis and microcirculation. Thus, REV-ERB agonism has a direct protection on the cardiomyocytes, consistent with our NRVM results in culture. Using RNA-Seq, we found that in NRVM SR9009-treated cells showed an enrichment in metabolic pathways that are known to be downregulated in HF, in particular fatty acid metabolism, which accounts for 70% of the energy source in the normal heart. Also, SR9009 has previously been reported to increase mitochondrial number, function, and mitophagy in skeletal muscle. We then investigated if there is a direct induction of mitochondria metabolism by SR9009. However, even after 10 weeks after TAC in the mouse hearts, there is no difference in mitochondria number estimated by mtDNA to nuclear DNA ratio, no difference in morphology by electron microscopy, and no difference in oxidative phosphorylation (OXPHOS) measured by oxygen consumption rate (Supplemental FIG. 1, E-G). These observations indicate that an improved energy metabolism is not the direct cause of REV-ERB-induced cardiac protection; rather, they support our cistrome and transcriptomic data that a pathological gene program is repressed in the cardiomyocytes.

We next sought to determine if REV-ERBα activation impacts the failing heart. Most interventions using animal models have focused on the outcome of disease prevention. However, patients often present with existing and sometimes late-stage HF; a potential therapy in human patients requires efficacy in treating established or even late-stage disease. To establish an HF model, we performed a 28-gauge TAC (more severe than the commonly used 27-gauge model) on a cohort of 18 mice (FIG. 4). At 2 weeks after TAC, we observed an average EF of 44%±1.3% in all the surviving mice (n=10). We randomized them into 2 groups based on EF and treated 1 group with Veh (Group I) and another with SR9009 (Group II). At 6 weeks after TAC, Group II maintained cardiac function, with an EF of 43.9%±5%, while Group I dropped to 29.1%±1.8% (P=0.01).

We then performed a cross-over, in which Group I received SR9009 and Group II received Veh, and we observed animals for an additional 5 weeks. Group I maintained an EF of 29.8%±3.7%, while Group II dropped to 17.5%±2.3% (P=0.01) (FIGS. 3, F and G). This result suggests that the REV-ERBα pathway can halt moderate and even severe HF. Finally, we investigated if a similar modulatory role of REV-ERBα exists in human cardiomyocytes.

We induced cellular hypertrophic response in human induced pluripotent stem cell-differentiated cardiomyocytes with endothelin-1 (ET-1) and monitored NPPB (BNP) expression with SR9009 or Veh pretreatment. Not too surprisingly, we observed a protective effect of SR9009, just as in the rodent cardiomyocytes (FIG. 5).

This example shows that REV-ERBα is a key regulator of cardiac pathological remodeling and ameliorates HF, both in a preventative and therapeutic fashion, in rodent models. Mechanistically, we demonstrated that REV-ERBα colocalizes with driver TFs, such as MEF2a and MEF2c, and represses aberrant gene expression during cardiac pathological stress.

Multiple TFs and chromatin remodeling factors have been shown to participate in the cardiac hypertrophy gene program. Using heart tissue ChIP-Seq, we have found that REV-ERBα can colocalize with driver TFs and coordinate transcription repression at thousands of loci in the genome mediated by multiple TFs, which can prevent pathogenic switch of gene program.

Several compounds have been generated to manipulate REV-ERB function. We chose to use SR9009 for its high efficacy and feasibility for in vivo studies. The specificity of SR9009 to REV-ERB has been shown to bind all 48 human nuclear receptors. Previously, SR9009 has been used in other studies and has demonstrated effects in shortening sleep, reducing anxiety, increasing skeletal muscle performance and endurance exercise, increasing oxygen consumption, and protecting against obesity induced by high fat diet. Due to its effect on mitochondria number, function, and mitophagy in skeletal muscle, as well as our GSEA results indicating an enriched expression in fatty acid metabolism, we tested the possibility of mitochondrial-driven cardiac protection. Our results indicate that there is no significant benefit directly associated with increased mitochondrial number or function. This difference may be due to tissue specificity or the particular type of injury being used. A more direct injury on the mitochondria, such as ischemia reperfusion, may induce more observable changes in the mitochondria.

Although pressure overload is a relatively heart-specific injury model, other systems and cell types may play a significant role in the outcome. We show that there is no difference in blood pressure, mitochondria number/morphology/oxidation and phosphorylation, capillary density, or CFs, suggesting that the SR9009-treated hearts had preserved cardiac function due to less cardiomyocyte injury instead of any secondary benefit from improved hemodynamics, metabolism, microcirculation, or less-reactive CFs. We conclude that REV-ERB activation has a direct protective effect in cardiomyocytes in a cell-autonomous fashion. We realize that fibrosis in vivo requires interaction between the cardiomyocytes and CFs, as well as other secretory factors.

We have shown that, in mice, the therapy is effective even in advanced disease at least to prevent disease progression—despite of the persisting insult. Its efficacy in advanced disease is particularly attractive to provide medical management to end-stage HF patients in order to avoid or delay heart transplant or mechanical assisting device.

While this invention has been shown and described with references to various embodiments thereof, it will be understood by those skilled in the art that changes in form and details may be made therein without departing from the scope of the invention encompassed by the appended claims. All patents, publications and references cited in the foregoing specification are herein incorporated by reference in their entirety.

What is claimed is:

1. A method of treating cardiac hypertrophy in a subject in need thereof, the method comprising:
   administering to the subject a therapeutically effective amount of a synthetic REV-ERBα agonist, the synthetic REV-ERBα agonist selected from the group consisting of 1,1-Dimethylethyl N-[(4-chlorophenyl) methyl]-N-[(5-nitro-2-thienyl)methyl])glycinate (SR6452); N-Benzyl-N-(4-chlorobenzyl)-1-(5-nitrothiophen-2-yl)methanamine; N-Benzyl-N-(3,4-dichlorobenzyl)-1-(5-nitrothiophen-2-yl)methanamine; 2-((4-chlorobenzyl)((5-nitrothiophen-2-yl)methyl)amino)-N,N-dimethylacetamide, ethyl 3-(((4-chlorobenzyl)((5-nitrothiophen-2-yl)methyl)amino)methyl)pyrrolidine-1-carboxylate (SR9009), 3-[[(4-chlorophenyl)methyl-[(5-nitrothiophen-2-yl)methyl]amino]methyl]-N-pentylpyrrolidine-1-carboxamide (SR9011), and pharmaceutically acceptable salts thereof.

2. The method of claim 1, the synthetic REV-ERBα agonist selected from the group consisting of SR9009 and SR6452.

3. The method of claim 1, wherein the synthetic REV-ERBα agonist is SR9009, and wherein the therapeutically effective amount is the amount required to inhibit an increase in left ventricle mass, left ventricle posterior wall thickness, intraventricular septum thickness or heart weight in the subject compared to a vehicle-treated control.

4. The method of claim 1, wherein the synthetic REV-ERBα agonist is SR9009, and wherein the therapeutically effective amount is the amount required to reduce cardiac fibrosis and/or cardiac cell death in the subject.

5. The method of claim 1, wherein the synthetic REV-ERBα agonist is administered to the subject by at least one of oral and/or parenteral delivery.

6. A method of treating cardiac hypertrophy in a subject in need thereof, the method comprising:
administering to the subject a therapeutically effective amount of SR9009, wherein the therapeutically effective amount is an amount effective to reduce cardiac fibrosis and/or cardiac cell death in the subject.

7. The method of claim 6, wherein the therapeutically effective amount is the amount required to inhibit an increase in left ventricle mass, left ventricle posterior wall thickness, intraventricular septum thickness or heart weight in the subject compared to a vehicle-treated control.

* * * * *